United States Patent [19]

Devon

[11] 4,328,379

[45] May 4, 1982

[54] HOMOLOGATION PROCESS

[75] Inventor: Thomas J. Devon, Kingsport, Tenn.

[73] Assignee: Eastman Kodak Company, Rochester, N.Y.

[21] Appl. No.: 252,752

[22] Filed: Apr. 10, 1981

[51] Int. Cl.$^3$ .................. C07C 29/00; C07C 27/00
[52] U.S. Cl. .............................. 568/902; 260/439 R
[58] Field of Search .......................................... 568/902

[56] References Cited

U.S. PATENT DOCUMENTS 3,248,432  4/1966  Riley et al. ..................... 568/902
4,126,752 11/1978  Novotny et al. ................. 568/902

Primary Examiner—Joseph E. Evans
Attorney, Agent, or Firm—J. Frederick Thomsen; Daniel B. Reece, III

[57] ABSTRACT

Disclosed is an improved process for the homologation of alkanols to obtain the next higher alkanol homolog by the cobalt-catalyzed reaction of an alkanol reactant with carbon monoxide and hydrogen under homologation conditions. The improvement comprises carrying out the homologation process in the presence of a perfluorocarboxylate anion.

4 Claims, No Drawings

HOMOLOGATION PROCESS

This invention relates to a novel process for homologating methanol to ethanol and ethanol to propanol in the presence of a cobalt catalyst. More particularly, this invention relates to the cobalt-catalyzed homologation wherein the homologation is carried out in the presence of a perfluorocarboxylate anion.

The homologation reaction wherein an alkanol, most often methanol, is reacted with carbon monoxide and hydrogen in the presence of a catalyst to obtain the next higher homolog of the alkanol reactant is well known. See, for example, U.S. Pat. Nos. 4,126,752, 4,133,966 and the references referred to therein. The most commonly used catalyst system comprises (1) a source of cobalt soluble in the reaction medium which will yield a cobalt carbonyl or hydrogen cobalt carbonyl under the reaction conditions employed and (2) an iodine compound, frequently referred to as a promoter, such as elemental iodine, an alkali metal iodide, an alkyl iodide or the like. Although the use of a cobalt-iodine catalyst system gives good conversions of methanol to acetaldehyde, the catalyst is not effective for hydrogenating acetaldehyde to ethanol. This results in the formation of significant amounts of acetaldehyde condensation products such as crotonaldehyde and higher molecular weight products. In an effort to overcome this problem, the use of additional catalyst components such as ligands and hydrogenation catalysts, for example, ruthenium, in combination with cobalt and iodine has been proposed. The use of such additional catalyst components can create other problems such as catalyst recovery, ligand decomposition, etc. which may detrimentally affect the economics of the overall homologation process.

I have discovered that in the cobalt catalyzed homologation of alkanols such as methanol and ethanol the alkanol can be converted in good selectivity to the next higher alkanol homolog if the homologation reaction is carried out in the presence of a catalytic amount of a perfluorocarboxylate anion and in the absence of essentially any iodine. The absence of essentially any iodine from the process is believed to permit the cobalt to effectively hydrogenate the aldehyde formed initially. The perfluorocarboxylate anion can be the residue of an alkyl, cycloalkyl or aryl carboxylic acid. Specific examples include perfluoroacetate (trifluoroacetate), perfluorooctonate (pentadecylfluorooctanoate), and perfluorobenzoate (pentafluorobenzoate). The source of the anion can be a cobalt salt such as cobalt perfluoroacetate, an ester such as methyl or ethyl ester of a perfluorocarboxylic acid or the perfluorocarboxylic acid itself may be used. Generally, the catalytic amount of perfluorocarboxylate anion used will be about 1,000 to 100,000 ppm based on the alkanol reactant fed. The amount which will give satisfactory results depends to some extent on the reaction conditions, the particular alkanol reactant and the particular perfluorocarboxylate anion employed. For most cases, anion concentrations of about 10,000 to 40,000 will give satisfactory results. The mole ratio of cobalt (as Co) to perfluorocarboxylate anion will not be more than about 8. The lower limit is not important, i.e. large amounts of anion per cobalt can theoretically be used, but usually there is no advantage in using a ratio of less than about 0.25.

The catalytic amounts of cobalt that can be used in the process of this invention normally will be in the range of about 1,000 to 14,000 ppm, preferably in the range of about 3,000 to 10,000. The source of the cobalt can be a cobalt perfluorocarboxylate, cobalt hydrate, cobalt acetylacetonate, dicobalt octacarbonyl, cobalt carbonate, cobalt acetate, etc. or mixtures thereof. The anion of the cobalt compound should not be one which will compete with the perfluorocarboxylate anion in the process and thus alter the catalytic effect of the latter. If desired, the catalyst system can contain additional components such as hydrogenation catalysts, e.g., ruthenium. However, as is indicated above, the use of significant amounts, e.g. over 100 ppm, of iodine in the catalyst system is not contemplated.

The homologation effective temperatures and pressures (total) that can be used can be varied substantially, e.g. over the ranges of about 150° to 250° C. and 1,000 to 10,000 psig. The preferred temperatures and pressures are in the ranges of about 170° to 210° C. and about 3,000 to 6,000 psig. The mole ratio of hydrogen to carbon monoxide fed to the homologation reactor also can be varied considerably, e.g. from 0.1 to 10, although, as is known in the art of homologation chemistry, the use of ratios in the upper part of that range is preferred to effect hydrogenation of the aldehyde initially formed. Under certain reaction conditions such as moderate pressures the gas must contain a certain minimum amount of carbon monoxide to avoid the formation of metallic cobalt which can plate out on the reactor walls and thus be lost from the system. The preferred hydrogen to carbon monoxide mole ratio therefore is in the range of about 1:1 to 3:1.

The invention is further illustrated by the following examples.

EXAMPLE 1—Synthesis of Cobaltous Trifluoroacetate Tetrahydrate

Trifluoroacetic acid (57.01 g.; 0.50 mole) was dissolved in 500 ml. of distilled water in a 1,000-ml. beaker with a magnetic stirrer. Cobaltous carbonate (35.68 g.; 0.30 mole) was added in small portions to the stirred acid solution over 15 minutes. The mixture was stirred an additional 5 minutes and then filtered by suction through a bed of celite to remove excess cobaltous carbonate and cobaltic oxide impurity. The bed was then washed with additional water. The red-violet clear filtrate was transferred to a two-liter roundbottom flask and stripped on a rotary evaporator heated by a steam bath until all liquid had set up to a wet violet crystalline mass. The flask was cooled to room temperature and placed on a vacuum pump. A pressure of 0.5 mm Hg was maintained for 4 hours to remove residual moisture from the product. The net weight of cobaltous trifluoroacetate tetrahydrate obtained was 90.74 g. Other cobaltous salts were obtained in similar procedures.

EXAMPLE 2—Preparation of Dicobalt Octacarbonyl

Cobaltous carbonate (30.0 g.) and 300 ml. of petroleum ether solvent were charged into a 1,000-ml. 316 stainless steel rocking autoclave. The autoclave was purged of air by pressuring to 100 psig with carbon monoxide and venting three times. The pressure was brought to 1700 psig with carbon monoxide and then raised to 3400 psig total pressure with hydrogen. The autoclave was heated to 150° C. and kept at 150° C. for 3 hours. The autoclave was cooled to room temperature and vented slowly. The solution was unloaded into a bottle under argon. The solution was filtered under argon. The filtrate was kept in a bottle under a carbon monoxide blanket and stored in the refrigerator to crystallize the product. The mother liquor was decanted from the crude product. The crystals were dried with a stream of carbon monoxide and stored under argon in petroleum ether in a sealed bottle in the refrigerator.

EXAMPLES 3-7—Methanol Homologation Reaction

Methanol (78.06 g.; 2.44 mole) was reacted with carbon monoxide and hydrogen using a 300-ml. Hastelloy B-2 autoclave. A Pyrex glass liner with a small Teflon, crown shaped magnetic stirrer, containing the methanol and catalyst was placed in the autoclave. The catalysts and the amounts of each used in Examples 3-7, respectively:

| Cobaltous perfluoroacetate tetrahydrate | 4.27 g. |
|---|---|
| Cobaltous perfluorooctonoate tetrahydrate | 11.48 g. |
| Cobaltous perfluorobenzoate tetrahydrate | 6.64 g. |
| Cobaltous iodide | 3.76 g. |
| Dicobalt octacarbonyl | 2.05 g. |

The catalysts were prepared as described above except the cobaltous iodide which was obtained from ROC/RIC Corporation.

A mixture of two-thirds hydrogen and one-third carbon monoxide was prepared in a high pressure surge tank. (A gas sample was taken for gas chromatographic analysis.) The autoclave was presured to 3,000 pounds per square inch gauge (psig) with the gas mixture and heated to 190° C. When the temperature reached 190° C., the pressure was adjusted to 5,000 psig. The reaction was allowed to proceed at 190° C. at 5,000 psig for 4 hours. The surge tank pressure was noted each hour. The autoclave was cooled to room temperature and vented. A sample of vent gas was collected half way through venting for gas chromatographic analysis. After venting was complete, the product was returned in the glass liner. A net weight of 100.05 g. of product was obtained. This was analyzed chromatographically.

In analyzing the liquid product the total weight of volatile components in the liquid product was calculated by subtracting the weight of cobalt salt charged in the run from the net weight of product. An assumption is made that all cobalt enters the gas chromatograph as the original salt or, in the case of cobalt carbonyl, as cobalt metal. The liquid samples were chromatographed on a 10'×⅛" 60/80 mesh Chromosorb 101 column in stainless steel using a Hewlett Packard 5730A gas chromatograph with a helium carrier and thermal conductivity detector. A temperature program used a heat up rate of 8° C./minute from an initial temperature of 70° to a final of 230° C.; a 4-minute hold was normally used at the upper limit. All major peaks were identified by spiking with pure known compounds. The sum of unknown peaks with retention times greater than that of ethanol were labeled as "unknown high boilers". The weight of each component in the product was calculated by multiplying the "weight of the volatile components" by the area percentage of that component in the product chromatograph and dividing by 100.

Table I shows the percent of methanol conversion (conv.) and the weight in g. of acetaldehyde (HAc), ethanol (EtOH), methyl acetate (MeOAc) and ethyl acetate (EtOAc) obtained in each example. By-products obtained included water, acetaldehyde dimethyl acetal, n-propanol, n-butanol, crotonaldehyde, methyl formate, "heavy" unknowns, and, in Example 6, a substantial amount of acetic acid (11.9 g.).

TABLE I

| Example | Conv. | HAc | EtOH | MeOAc | EtOAc |
|---|---|---|---|---|---|
| 3 | 63 | 1.9 | 21.0 | 4.2 | 1.8 |
| 4 | 51 | 0.9 | 14.2 | 8.0 | 1.6 |
| 5 | 58 | 1.1 | 23.8 | 7.7 | 4.9 |
| 6 | 88 | 3.5 | 0.7 | 19.1 | 1.0 |
| 7 | 33 | 0.3 | 12.8 | 1.4 | 0.0 |

EXAMPLE 8

To a 1-liter Hastelloy-B autoclave equipped with a Hastellloy-B clad stirrer was charged cobaltous trifluoroacetate tetrahydrate (30.2 g.) and methanol (549.2 g.). The autoclave was sealed, purged with nitrogen and then pressurized to 2000 psig with a 1:1 mixture of hydrogen and carbon monoxide. The contents of the autoclave were heated to 190° C. and a sample of the reaction mixture was collected via a dip tube in the autoclave. The pressure then was raised to 4000 psig using the same gas mixture. Liquid samples were taken every 30 minutes while the reaction was carried out at 190° C. and 4000 psig over a period of 4 hours. The autoclave was cooled to room temperature and vented to atmospheric pressure.

The total weight of liquid product was 727.3 g. or 697.1 g. of volatile compounds after subtracting out the weight of non-volatiles for a weight gain of 148 g. The total weight of volatile products at any of the sampling times is estimated by assuming a linear weight gain throughout the progression of the run at 190° C. Thus, the weight of volatile components at 2.5 hours into the run is estimated to be 641.7 g. The weight of each product compound was calculated using the above volatile weight as a basing and using the chromatographic and calculation procedure employed in Examples 3-7.

The composition of the reaction mixture in grams obtained after 2.5 hours at reaction conditions is shown in Table II. The reaction mixture was made up of unreacted methanol (MeOH), acetaldehyde, ethanol, methyl acetate, n-propanol (PrOH), acetaldehyde dimethyl acetal (ADMA), ethyl acetate, crotonaldehyde (CrHO), heavy unknowns (HU) and water.

EXAMPLE 9

The procedure of Example 8 was repeated using as the catalyst a 1:1 mole ratio of cobaltous acetonylacetate (21.6 g.) and iodine (21.3 g.). The liquid product sample taken at 3 hours and thereafter became two phase. The weight of each product component, set forth in Table II, for the sample taken after 2.5 hours was calculated as in Example 8. The starting weight of volatiles was 547.3 g., the final weight was 776.6 g. and the weight of volatile products at 2.5 hours is estimated at 690.6 g.

EXAMPLE 10

The procedure of Example 8 was repeated using as the catalyst a 1:1 mole ratio of cobaltous perfluoroacetate tetrahydrate (15.0 g.) and cobaltous acetonylacetate (10.8 g.). The weight of each product component, set forth in Table II, for the sample taken after 2.5 hours was calculated as in Example 8. The starting weight of volatiles was 551.9 g., the final weight was 701.7 g. and the weight of volatile products at 2.5 hours is estimated to be 645.5 g.

In Examples 8-10 the reaction mixture composition was determined after 2.5 hours at reaction conditions because in Example 9 the reaction mixture, because of high boiler formation, became heterogenous and could not be analyzed by the technique described.

TABLE II

|       | Example 8 | Example 9 | Example 10 |
|-------|-----------|-----------|------------|
| MeOh  | 340.9     | 178.7     | 346.9      |
| HAc   | 6.8       | 22.1      | 4.9        |
| EtOH  | 86.7      | 39.5      | 89.1       |
| MeOAc | 14.6      | 59.8      | 19.0       |
| PrOH  | 3.4       | 0.0       | 4.7        |
| ADMA  | 14.4      | 24.1      | 16.0       |
| EtOAc | 1.3       | 10.6      | 1.8        |
| CrH   | 0.6       | 13.1      | 0.9        |
| HU    | 14.0      | 54.0      | 14.6       |
| $H_2O$ | 153.8    | 277.6     | 143.9      |

EXAMPLE 11

Absolute ethanol (78.43 g.) and cobaltous trifluoroacetate tetrahydrate (4.30 g.) were charged to a 300 ml. autoclave system as described in Examples 3-7. The autoclave was pressurized to 3000 psig with a 1:1 mole ratio mixture of hydrogen and carbon monoxide at room temperature and then heated to 190° C. At 190° C. the pressure was brought to 5000 psigg with the same gas mixture and the reaction was carried out under these conditions for four hours. After cooling to room temperature the mixture was vented and the liquid product mixture removed from the autoclave. A total weight of 86.79 g. of product was obtained or a yield of 82.49 g. of volatiles. The volatile product mixture was analyzed via gas chromatography using the procedure described in Examples 3-7. The run had an ethanol conversion of 14% and produced water (6.1 g.), propionaldehyde (0.7 g.), n-propanol (3.7 g.), ethyl propionate (0.1 g.) and a total weight of unknown compounds (3.6 g.).

Although the invention has been described in considerable detail with particular reference to certain preferred embodiments thereof, variations and modifications can be effected within the spirit and scope of the invention.

I claim:

1. In the process for the homologation of methanol to ethanol and ethanol to propanol by the reaction of methanol and/or ethanol with hydrogen and carbon monoxide in the presence of a cobalt catalyst at an elevated temperature and pressure, the improvement comprising carrying out the reaction in the presence of a perfluorocarboxylate anion and in the absence of essentially any iodine.

2. Process according to claim 1 wherein the mole ratio of cobalt to perfluorocarboxylate anion is about 0.25 to 8.0.

3. Process for the homologation of methanol to ethanol by contacting methanol with a mixture of hydrogen and carbon monoxide at a temperature of about 150° to 250° C. and a pressure of about 1,000 to 10,000 psig in the presence of a catalytic amount of a cobalt catalyst and a catalytic amount of a perfluorocarboxylate anion and in the absence of essentially any iodine.

4. Process of claim 3 wherein the mole ratio of hydrogen and carbon monoxide used is about 1:1 to 1:3, the temperature is about 170° to 210° C., the pressure is about 3,000 to 6,000 psig, the catalytic amount of cobalt is about 3,000 to 10,000 ppm and the cobalt to perfluorocarboxylate mole ratio is about 0.25 to 8.

* * * * *